US012789851B2

(12) United States Patent
Cassebaum et al.

(10) Patent No.: US 12,789,851 B2

(45) Date of Patent: Nov. 10, 2026

(54) AUDIO SIGNAL PROCESSING FOR DETECTING RESPIRATORY DISEASE

(71) Applicant: Volkswagen Aktiengesellschaft, Wolfsburg (DE)

(72) Inventors: Oliver Cassebaum, Wolfsburg (DE); Steffen Mölle, Magdeburg (DE); Hans-Georg Nitzke, Wettmershagen (DE); Andreas Udo Sass, Hannover (DE); Dirk Pohnert, Wolfsburg (DE); Jan Piewek, Magdeburg (DE)

(73) Assignee: Volkswagen Aktiengesellschaft, Wolfsburg (DE)

(*) Notice: Subject to any disclaimer, the term of this patent is extended or adjusted under 35 U.S.C. 154(b) by 151 days.

(21) Appl. No.: 18/567,273

(22) PCT Filed: May 12, 2022

(86) PCT No.: PCT/EP2022/062941
§ 371 (c)(1),
(2) Date: Mar. 21, 2024

(87) PCT Pub. No.: WO2022/258302
PCT Pub. Date: Dec. 15, 2022

(65) Prior Publication Data

US 2024/0262388 A1 Aug. 8, 2024

(30) Foreign Application Priority Data

Jun. 11, 2021 (DE) ........................ 102021205970.8

(51) Int. Cl.

| | |
|---|---|
| ***B60W 60/00*** | (2020.01) |
| ***B60W 40/08*** | (2012.01) |
| *A61B 5/00* | (2006.01) |

(52) U.S. Cl.
CPC ........ *B60W 60/0016* (2020.02); *B60W 40/08* (2013.01); *A61B 5/4803* (2013.01);
(Continued)

(58) Field of Classification Search
CPC ............. B60W 60/0016; B60W 40/08; B60W 2040/089; B60W 2540/21; B60W 2540/221; A61B 5/4803; A61B 7/003
See application file for complete search history.

(56) References Cited

U.S. PATENT DOCUMENTS

| | | | |
|---|---|---|---|
| 5,309,922 A | 5/1994 | Schechter et al. | |
| 8,738,523 B1 * | 5/2014 | Sanchez | G06Q 40/00 705/4 |

(Continued)

FOREIGN PATENT DOCUMENTS

| | | | |
|---|---|---|---|
| CA | 3024698 A1 | 5/2020 | |
| CN | 104276037 A * | 1/2015 | B60W 50/12 |

(Continued)

OTHER PUBLICATIONS

PCT/EP2022/062941 International Search Report (Jul. 15, 2022).
Priority German Application No. 102021205970.8. Office Action (May 28, 2024).

*Primary Examiner* — Redhwan K Mawari
(74) *Attorney, Agent, or Firm* — Peter Zura; LOZA & LOZA, LLP

(57) ABSTRACT

Technologies and techniques for detecting a disease for use within a motor vehicle. An audio signal of a driver is recorded over time, and a characteristic temporal sequence of the audio signal is selected in order to perform a time-resolved analysis of the audio signal. The audio signal is processed within the selected characteristic temporal sequence with a comparison signal in order to determine differences between the audio signal and the comparison signal. A diagnosis is generated based on the comparison
(Continued)

between the audio signal and the comparison signal, the comparison between the audio signal and the comparison signal being performed via a time-resolved frequency analysis.

20 Claims, 4 Drawing Sheets

(52) U.S. Cl.
CPC ... *B60W 2040/089* (2013.01); *B60W 2540/21* (2020.02); *B60W 2540/221* (2020.02)

(56) References Cited

U.S. PATENT DOCUMENTS

| | | | | |
|---|---|---|---|---|
| 10,627,817 | B2 * | 4/2020 | Zijderveld | G08G 1/0129 |
| 10,779,761 | B2 * | 9/2020 | el Kaliouby | G08G 1/0962 |
| 10,796,176 | B2 * | 10/2020 | el Kaliouby | G06F 18/2414 |
| 10,897,650 | B2 * | 1/2021 | el Kaliouby | A61B 5/18 |
| 10,922,567 | B2 * | 2/2021 | Mahmoud | G08G 1/0129 |
| 11,067,405 | B2 * | 7/2021 | Fouad | G05D 1/0061 |
| 11,404,074 | B2 * | 8/2022 | Kirsch | G10L 25/30 |
| 2010/0228460 | A1 * | 9/2010 | Saito | B60T 7/12 701/70 |
| 2015/0120336 | A1 * | 4/2015 | Grokop | H04R 3/002 705/4 |
| 2015/0125126 | A1 * | 5/2015 | Dreuw | G08B 21/06 386/226 |
| 2016/0361999 | A1 * | 12/2016 | Raz | B60W 40/08 |
| 2017/0135620 | A1 | 5/2017 | Bae et al. | |
| 2020/0279345 | A1 * | 9/2020 | Jiwani | G06Q 10/063112 |

FOREIGN PATENT DOCUMENTS

| | | | | |
|---|---|---|---|---|
| CN | 109009125 | A | | 12/2018 |
| CN | 110853620 | A | | 2/2020 |
| CN | 111493897 | A | | 8/2020 |
| CN | 112309423 | A | | 2/2021 |
| DE | 102014003783 | A1 | | 9/2015 |
| DE | 112015001807 | B4 | | 4/2019 |
| JP | H09173320 | A | * | 7/1997 |
| JP | 2018032339 | A | | 3/2018 |
| JP | 2018126511 | A | | 8/2018 |
| JP | 2020173836 | A | | 10/2020 |
| WO | 2018168369 | A1 | | 9/2018 |
| WO | 2020188623 | A1 | | 9/2020 |
| WO | 2022004887 | A1 | | 1/2022 |

* cited by examiner

AUDIO SIGNAL PROCESSING FOR DETECTING RESPIRATORY DISEASE

RELATED APPLICATIONS

The present application claims priority to International Patent Application No. PCT/EP2022/062941 to Cassebaum et al., filed May 12, 2022, titled "Method for Diagnosing a Disease, Preferably a Respiratory Disease," which claims priority to German Pat. App. No. DE 10 2021 205 970.8, filed Jun. 11, 2021, to Cassebaum et al., the contents of each being incorporated by reference in their entirety herein.

TECHNICAL FIELD

The present disclosure relates to a method and to a system for detecting a disease, such as a respiratory disease for application or for use in a motor vehicle. The present disclosure furthermore relates to a motor vehicle incorporated the system for detecting disease.

BACKGROUND

Methods and systems for diagnosing diseases are known from the prior art. However, the known solutions can essentially only be carried out on an in-patient basis in a laboratory and are consequently tied to the prior arrangement of appointments. The cumbersome nature of arranging appointments in advance and the effort of having to visit a laboratory for the methods to be carried out deter a large number of patients from undergoing examinations regarding potential diseases.

Even though methods for detecting a current physical condition are known from WO 2020/188623 A1 and CA 3 024 698 A1, which are also intended to diagnose heart attacks or strokes in a mobile manner within a motor vehicle, for example, the known methods are predominantly provided to detect an unfitness to drive, and therefore to ensure driving safety, and not to diagnose diseases. The known methods, in contrast, are not suitable for precisely diagnosing diseases, in particular respiratory diseases, due to a lack of sensitive measuring technology and data analysis.

SUMMARY

Aspects of the present disclosure are directed to addressing at least some of the above-described disadvantages of methods and systems for detecting or diagnosing diseases, preferably respiratory diseases, and providing technologies and techniques for detecting such diseases in a simple, rapid and comfortable manner.

Some aspects of the present disclosure are provided in the subject matters of the independent claims, found below. Other aspects are disclosed in the subject matter of the respectively associated dependent claims.

In some aspects, technologies and techniques disclosed herein for detecting/diagnosing a disease, preferably a respiratory disease, can be used in vehicles driven by internal combustion engines as well as in electric or hybrid vehicles. In addition to being used in motor vehicles, such as passenger cars or trucks, aspects of the present disclosure can also be used in commercial vehicles, as well as autonomously controllable or autonomously controlled vehicles.

In some examples, a method for detecting/diagnosing a disease is disclosed for use within a motor vehicle, comprising recording an audio signal of a driver of the motor vehicle over a time, selecting a characteristic chronological sequence of the audio signal for carrying out a time-resolved analysis of the audio signal, and comparing the audio signal within the selected characteristic chronological sequence to a comparison signal for ascertaining differences between the audio signal and the comparison signal. Moreover, the method according to the present disclosure comprises the step of making a diagnosis based on the comparison between the audio signal and the comparison signal, wherein the comparison between the audio signal and the comparison signal is carried out via a time-resolved frequency analysis.

It should be understood by persons having ordinary skill in the art that individual, combined, or all mandatory and/or optional steps of the method disclosed herein can be carried out in the proposed order, but also deviating from the proposed order. Individual, combined, or all mandatory and/or optional steps of the method disclosed herein may also be performed repeatedly or repeatedly in cycles. It shall furthermore be understood that individual, several or all of the mandatory and optional steps of the method according to the invention in the present invention can also be implemented by a computer.

In some examples, a system is disclosed for detecting/diagnosing a disease within a motor vehicle, using any of the method steps disclosed herein. The system may comprises an audio signal recording unit for recording an audio signal of a driver of the motor vehicle over a time, a processing unit for selecting a characteristic chronological sequence of the audio signal and for comparing the audio signal within the selected characteristic chronological sequence to a comparison signal, and an evaluation unit for making a diagnosis based on the comparison, wherein the processing unit is designed in such a way that the comparison of the audio signal to the comparison signal can be carried out by means of the processing unit in the form of a time-resolved frequency analysis. The system according to the present disclosure thus has the same advantages as those that were already described in detail with respect to the method according to the present disclosure.

Aspects of the present disclosure likewise relate to a motor vehicle, comprising a system configured in any manner described in the examples and embodiments provided herein.

In some examples, a computer program product is disclosed, encompassing commands that, when the computer program is being executed by a processing device, and in particular the processing unit and/or the evaluation unit of the present motor vehicle, prompt the processing device, processing unit and/or evaluation unit to carry out the steps of the method according to the present disclosure. The computer program product according to the present disclosure thus entails the same advantages as those that were described in detail with respect to a method or the system disclosed herein.

Additional advantages, features and details will be apparent from the following description, which in detail describes exemplary embodiments with reference to the drawings. The features described in the claims and in the description may be considered essential to the present disclosure either alone or in any arbitrary combination.

DETAILED DESCRIPTION

Figure 1:
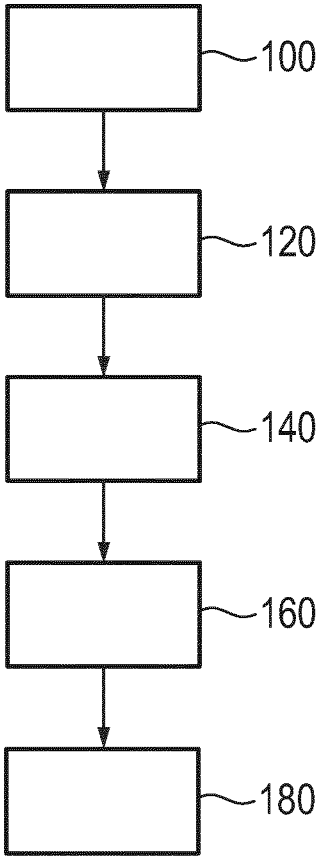
FIG. 1 shows a schematic representation of the individual steps of a method for detecting/diagnosing a disease for use within a motor vehicle, according to some aspects of the present disclosure.

As disclosed herein, detecting/diagnosing a respiratory disease may be understood to mean recognizing or making the finding of a disease in the area of the respiratory tract, such as asthma, bronchitis, sinusitis, influenza, laryngitis, tonsillitis, and in particular respiratory diseases caused by infections by viruses, such as RSV, SARS-COV, Covid-19 or the like. According to the present disclosure, recording an audio signal may be understood to mean receiving and storing a sound signal or an electrical signal in the perceptible frequency range of the human ear. An audio signal may, for example, encompass the change in the frequency and/or in the acoustic power or the sound pressure level over the time. The recording of an audio signal provided according to the present disclosure can preferably be started by being "triggered" by certain words, such as, for example, by a name being spoken, similarly to "Alexa" or "Siri" or the like. The recording of the audio signal can, for example, be started two seconds before the trigger word ("pre-trigger") and extend until the end of the spoken word, or it may extend up to an arbitrarily definable time after the end of the word.

It should be understood that, under the present disclosure, a "driver" as referred to herein can also be understood to mean a front-seat passenger or an occupant of a motor vehicle. For example, the present method can also be used to diagnose diseases of passengers in buses, trains or taxis, or the like, for example. In some examples, a characteristic chronological sequence of the audio signal may be understood to mean a time segment or a certain discrete point in time, which may be particularly characteristic or meaningful for diagnosing a disease. In some examples, the comparison signal disclosed herein may be configured in the form of a comparison library, in particular based on historical data, and serve to recognize drifts or breaks.

The stored signal or the comparison library can advantageously stem from the same person for which the diagnosing is to be carried out and can have been recorded under the same conditions that were present while the method is carried out. For example, the same background or ambient noise may be present. In particular, the comparison signal can be recorded over the same time period and, for example, can encompass the same words or word sequences of a driver. Within the scope of the present disclosure, a time-resolved analysis may be understood to mean an analysis that relates to a certain, preferably selected time frame, or point in time. A time-resolved frequency analysis can accordingly be understood to mean an analysis of the frequency profile within a certain, preferably selected time frame, or point in time. When using a time frame, a corresponding integration can be carried out over the time frame with respect to the recorded frequencies. The comparison between the audio signal and the comparison signal can preferably comprise a transformation of the recorded audio signal by means of a Fourier transform, and in particular by means of a Fast Fourier transform (FFT).

One skilled in the art will appreciate that that diagnosing diseases under the present disclosure can be carried out in a simple, rapid and reliable manner by analyzing audio signals. A surrounding area of a motor vehicle is particularly well-suited for detecting diseases by analyzing audio signals. Carrying out the methods within a motor vehicle not only offers the advantage that recurring ambient conditions, such as known constant acoustics having constant ambient noise, can be advantageously utilized, but the audio signals can also encompass known, frequently used voice commands. Using reliably predictable audio patterns, a characteristic chronological sequence of audio signal may be obtained for selection.

Audio signals reflects the change in the frequency and/or in the sound pressure level over time. With respect to reliably diagnosing a disease by way of a comparison between a characteristic chronological sequence of an audio signal and a comparison signal, it has shown to be effective to record, within the audio signal, the profile of the frequency and/or the profile of the sound pressure level against the time. Both the frequency and the sound pressure level have shown to be effective variables for diagnosing a disease.

The audio signal may reflect a change in the frequency and in the sound pressure level over time, and comparison of the audio signal to the comparison signal includes detecting or determining differences with respect to the profile of the sound pressure level with varying frequency within the selected characteristic chronological sequence.

The characteristic chronological sequence of the audio signals may correspond to at least a portion of a word and/or of a word sequence of the driver of the motor vehicle, wherein the word and/or the word sequence are preferably designed in the form of an input command of the driver. Using a word or a word sequence, such as a verbal input command of a driver, additionally offers the advantage that recurring ambient conditions, such as known constant acoustics having constant ambient noise, can be utilized, and the audio signals can also encompass known, frequently-used voice commands. Thus, the same words, word sequences, and forms of voice commands may be used for the comparison signals. Advantageously, the comparison signals can be configured in the form of recorded voice commands, or voice command sequences, of the person to be examined.

Thus, a simple and rapid option of diagnosing a disease is provided by way of a comparison between a characteristic chronological sequence of an audio signal and a comparison signal. It may furthermore be provided in the present disclosure that the characteristic chronological sequence of the audio signal may correspond to a specific discrete point in time. The use of a specific discrete point in time, serving as the characteristic chronological sequence, may be an advantageous choice for audio signals, based on which of a characteristic chronological sequence or the characteristic point in time can be precisely determined, for example in a voice command having a characteristic frequency or sound pressure level profile.

In some examples, the comparison of the audio signal to the comparison signal may be carried out in a specific frequency band or section, and preferably at a specific frequency, wherein the sound pressure level of the audio signal and of the comparison signal is compared.

So as enable reliable diagnosing in a simple and rapid manner, it is furthermore advantageous when the values of the audio signal and/or of the comparison signal are processed prior to the comparison of the audio signal to the comparison signal, wherein the processing preferably comprises a standardization of the values of the audio signal and/or of the comparison signal.

With respect to an intervention that is as anticipatory as possible when diagnosing a disease, it is furthermore conceivable that protective measures are initiated as a function of the diagnosis made, wherein the protective measures comprise informing the driver of the motor vehicle and/or activating a supporting driving mode, in particular an autonomous driving cycle and/or initiating an emergency stop and/or making an emergency call and/or changing a passenger compartment climate and/or disinfecting the vehicle.

In some examples, voice recognition may be utilized to identify a person, based on the recorded audio signal.

FIG. 1 shows a schematic representation of the individual steps of a method according to the present disclosure for detecting/diagnosing a disease for use within a motor vehicle 80.

According to the present method, first an audio signal AS of a driver of the motor vehicle 80 over a time T is recorded, and a characteristic chronological sequence S of the audio signal AS is selected 120 for carrying out a time-resolved analysis of the audio signal AS.

In this example, the audio signal AS within the selected characteristic chronological sequence S is compared 140 to a comparison signal VS to ascertain differences between the audio signal AS and the comparison signal VS.

Before the audio signal AS is compared 140 to the comparison signal VS, the values of the audio signal AS and/or of the comparison signal VS may be processed, wherein the processing may comprise a standardization of the values of the audio signal AS and/or of the comparison signal VS.

The comparison 140 of the audio signal AS to the comparison signal VS can be carried out in a specific frequency band or section $F_A$, preferably at a specific frequency $F_S$, wherein in particular the sound pressure level SPL of the audio signal AS and of the comparison signal VS can be compared.

After the audio signal AS has been compared 140 to the comparison signal VS, a diagnosis is made 160 based on the comparison 140 between the audio signal AS and the comparison signal VS, wherein the comparison 140 between the audio signal AS and the comparison signal VS may be carried out via a time-resolved frequency analysis.

Thereafter, protective measures are initiated 180 as a function of the diagnosis made, wherein the protective measures can comprise informing a driver of the motor vehicle 80 and/or activating a supporting driving mode, in particular an autonomous driving cycle and/or initiating an emergency stop and/or making an emergency call and/or changing a passenger compartment climate and/or disinfecting the vehicle.

Figure 2:
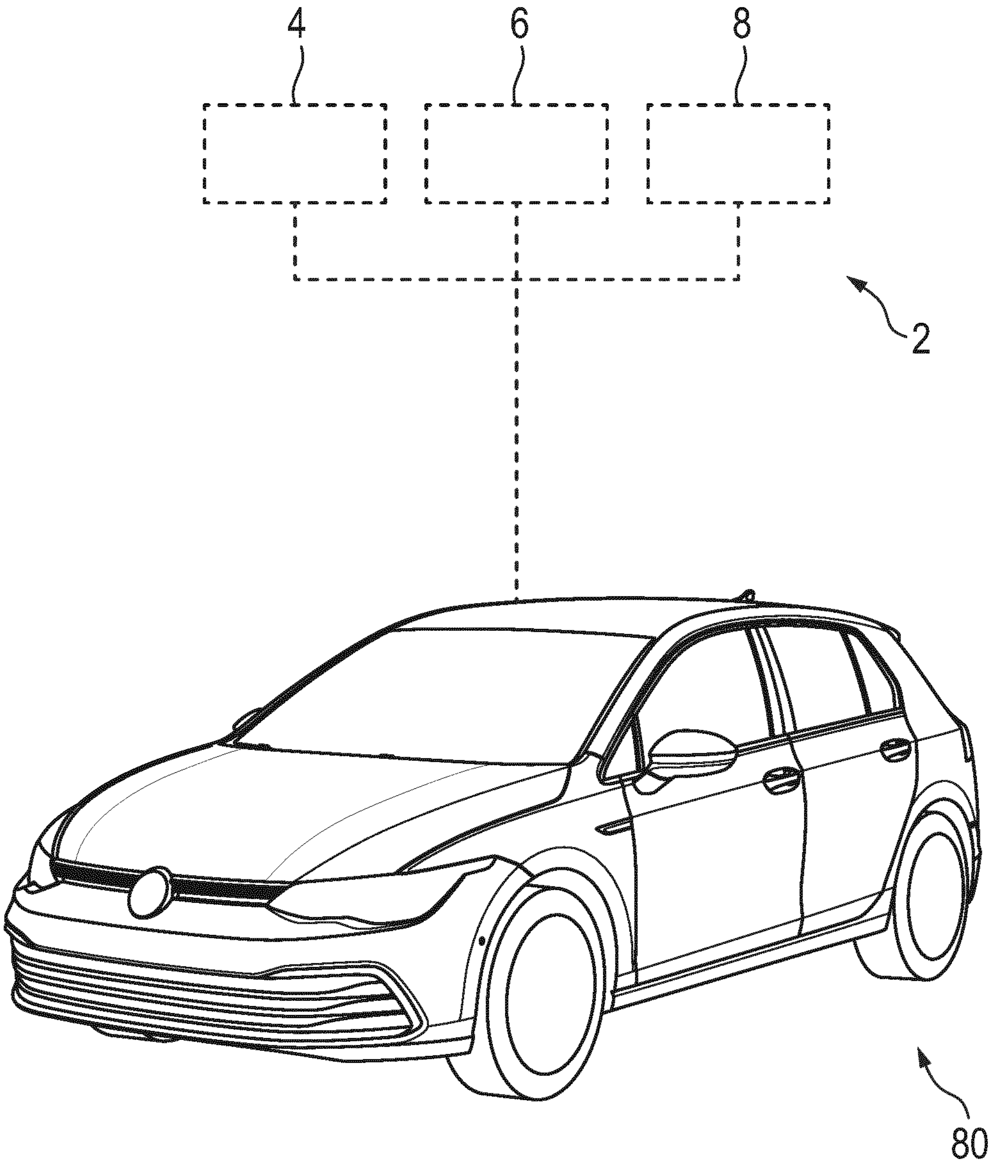
FIG. 2 shows a schematic representation of components of a system for diagnosing a disease within a motor vehicle, according to some aspects of the present disclosure.

FIG. 2 shows a schematic representation of the essential components of a system 2 according to some aspects of the present disclosure for diagnosing a disease within a motor vehicle 80. The system 2 can be fixedly installed in the motor vehicle or may also be used as a separate component in different vehicles 80.

The system 2 comprises an audio signal recording unit 4 for recording 100 an audio signal AS of a driver of the motor vehicle 80 over a time T, a processing unit 6 for selecting 120 a characteristic chronological sequence S of the audio signal AS and for comparing 140 the audio signal AS within the selected characteristic chronological sequence S to a comparison signal VS, and an evaluation unit 8 for making 160 a diagnosis based on the comparison 140. The processing unit 6 is designed in such a way that the comparison 140 of the audio signal AS to the comparison signal VS can be carried out by means of the processing unit 6 in the form of a time-resolved frequency analysis.

Figure 3:
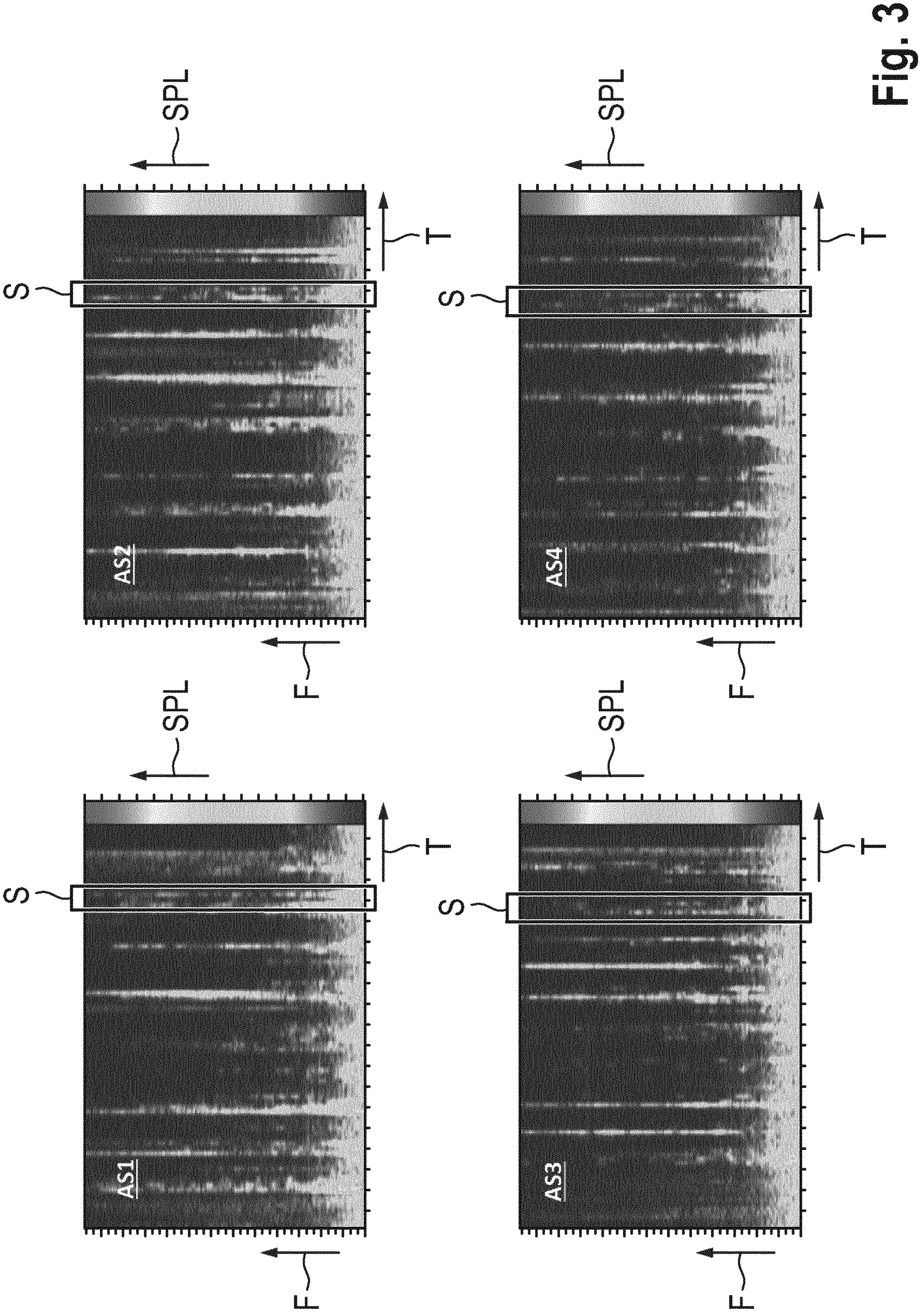
FIG. 3 shows a schematic representation of different audio signals of a driver of a motor vehicle over time, according to some aspects of the present disclosure.

FIG. 3 shows a schematic representation of various audio signals AS1 to AS4 of a driver of a motor vehicle 80 over a time T (FFT vs time).

In the present example, the audio signals AS1 to AS4 reflect the change in the frequency F and in the sound pressure level SPL over the time T. In the present example, the respective selected characteristic chronological sequence S of the audio signals AS1 to AS4 corresponds to a word sequence of an input command of the driver, such as, for example, the command “radio on.” As an alternative to a characteristic chronological sequence S of the audio signal AS in the form of a time frame, the characteristic chronological sequence S may also correspond to a specific discrete point in time $T_D$. In the present example, the audio signal AS1 shall be regarded as the comparison signal VS. It may be designed, for example, in the form of a stored recording of an audio signal, preferably of the same person (driver, front-seat passenger, occupant) for whom the diagnosing or the method according to the present disclosure is to be carried out. The comparison signal VS was accordingly preferably recorded under the same conditions as the audio signals AS2 to AS4, which each reflect audio signals in which, due to a disease, for example a pressure on the larynx is present (AS2) or the nose is congested (AS3, AS4).

Figure 4:
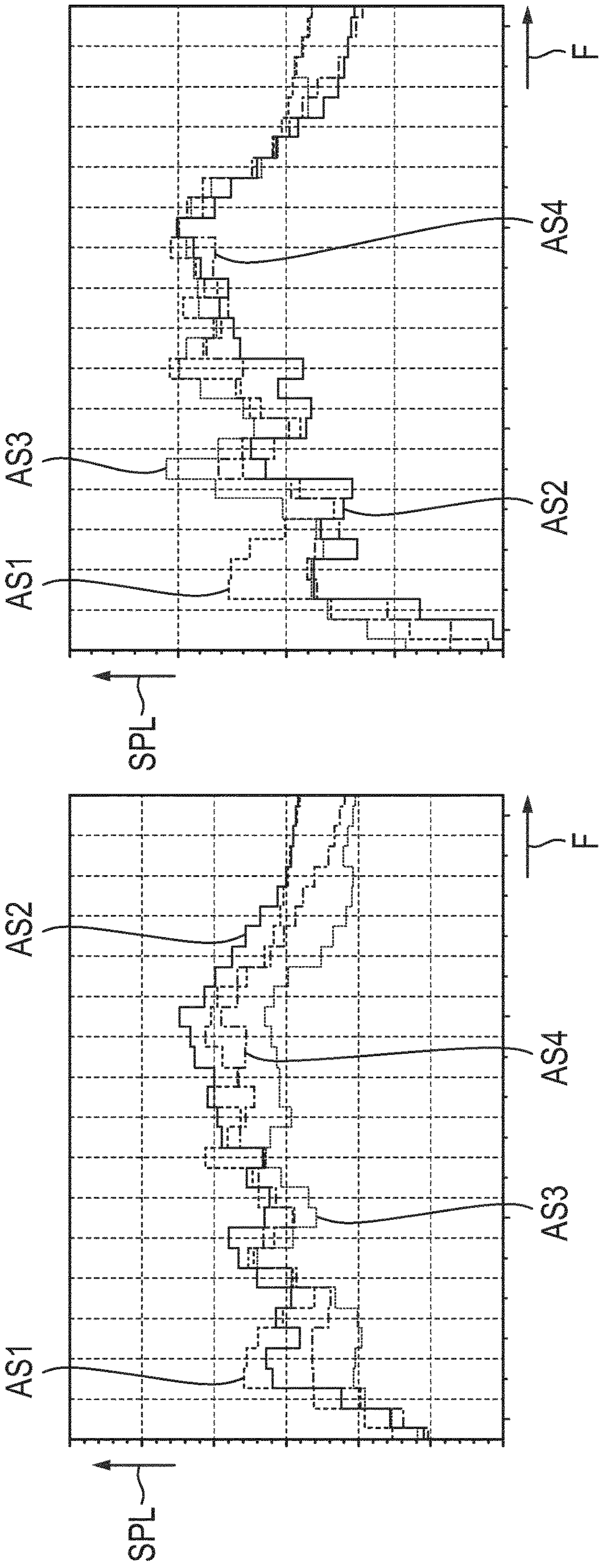
FIG. 4 shows a schematic representation of a comparison of the audio signals from FIG. 3 within a selected characteristic chronological sequence in an unprocessed state (left) and a processed state (right), according to some aspects of the present disclosure.

FIG. 4 shows a schematic representation of a comparison of the audio signals from FIG. 3 within the selected characteristic chronological sequence S in an unprocessed state (left) and in a processed state (right), wherein the audio signals AS1 to AS4 from FIG. 3 in the present example are shown in a time-resolved manner, and the change in the sound pressure level SPL for the audio signals AS1 to AS4 is shown with the change in the frequency F within the selected characteristic chronological sequence S. It shall be understood that the values of the sound pressure level SPL and of the frequency F, when selecting a time frame in contrast to a discrete point in time $T_D$, can be integrated over the time frame. In contrast to the unprocessed representation of the time-resolved audio signals AS1 to AS4 on the left side, the audio signals AS1 to AS4 shown on the right side are illustrated in standardized form. As can be shown based on the representation, the audio signals AS2 to AS4, in which a disease is present, can be distinguished, after appropriate processing, from the comparison signal (AS1) in a time-resolved representation in a selected characteristic chronological sequence in a simple and reliable manner.

Using the method and the system 2 according to the present disclosure for diagnosing a disease, it is thus possible by means of a time-resolved analysis of an audio signal within a motor vehicle to reliably diagnose a disease in a simple, rapid and comfortable manner.

The above description of the embodiments exclusively describes the present disclosure based on examples. If technically expedient, individual features of the embodiments can, of course, be freely combined with each other without departing from the scope of the present disclosure.

LIST OF REFERENCE SIGNS

2 system for diagnosing a disease
4 audio signal recording unit

6 processing unit
8 evaluation unit
80 motor vehicle
100 recording an audio signal
120 selecting a characteristic chronological sequence of the audio signal
140 comparing/comparison of the audio signal to the comparison signal
160 making a diagnosis based on the comparison between the audio signal and the comparison signal
180 initiating protective measures
AS audio signal
T time
$T_D$ specific discrete point in time
S characteristic chronological sequence
VS comparison signal
F frequency
$F_A$ specific frequency section
$F_S$ specific frequency
SPL sound pressure level

The invention claimed is:

1. A method for activating a protective measure in a vehicle based on a detection of a disease within a vehicle, comprising:

recording, by the vehicle, an audio signal relating to a driver of the vehicle over a time, the audio signal being generated by at least one microphone of the vehicle;

selecting, by at least one processor of the vehicle, a characteristic chronological sequence of the audio signal for executing a time-resolved analysis;

performing, by the at least one processor, a time-resolved frequency transform of the audio signal within the selected characteristic sequence and computing a difference metric between the transformed audio signal and a stored comparison signal previously recorded from the same driver;

detecting, by the at least one processor, a disease based on the computed difference metric; and causing a vehicle control system to activate a vehicle-implemented protective measure in response to the detected disease.

2. The method according to claim 1, wherein the audio signal comprises data indicating the change in the frequency and/or in the sound pressure level over the time.

3. The method according to claim 1, wherein the audio signal comprises data reflecting the change in the frequency and in the sound pressure level over the time, and wherein the comparing of the audio signal to the comparison signal comprises determining differences with respect to a profile of the sound pressure level with varying frequency within the selected characteristic chronological sequence.

4. The method according to claim 1, wherein the characteristic chronological sequence of the audio signal corresponds to at least a portion of a word and/or a word sequence of the driver of the motor vehicle associated with a verbal input command of the driver.

5. The method according to claim 1, wherein the characteristic chronological sequence of the audio signal corresponds to specific discrete points in time.

6. The method according to claim 1, wherein the comparing of the audio signal to the comparison signal is carried out in one of (i) a specific frequency section, (ii) a specific frequency, or (iii) a sound pressure level of the audio signal and the comparison signal being compared.

7. The method according to claim 1, further comprising standardizing the values of the audio signal and/or the comparison signal before the audio signal is compared to the comparison signal.

8. The method according to claim 1, wherein protective measure is initiated as a function of the detecting of the disease, the protective measure comprising one or more of (i) activating a notification in a system of the vehicle, (ii) activating a supporting driving mode, (iii) initiating an emergency stop, (iv) making an emergency call, (v) changing a passenger compartment climate, and/or (vi) disinfecting the vehicle.

9. The method according to claim 1, further comprising executing voice recognition to identify the driver, based on the recorded audio signal.

10. A system for activating a protective measure in a vehicle based on a detection of a disease within a vehicle, comprising:

at least one microphone of the vehicle configured to generate an audio signal relating to a driver of the vehicle over a time;

at least one processor of the vehicle, operatively coupled to the at least one microphone, wherein the at least one processor processing unit is configured to select a characteristic chronological sequence of the audio signal for executing a time-resolved analysis of the audio signal;

perform a time-resolved frequency transform of the audio signal within the selected characteristic sequence and compute a difference metric between the transformed audio signal and a stored comparison signal previously recorded from the same driver;

detect a disease based on the computed difference metric; and a vehicle control system operatively coupled to the at least one processor and configured to activate a vehicle-implemented protective measure in response to the detected disease.

11. The system according to claim 10, wherein the audio signal comprises data indicating the change in the frequency and/or in the sound pressure level over the time.

12. The system according to claim 10, wherein the audio signal comprises data reflecting the change in the frequency and in the sound pressure level over the time, and wherein the processing unit is configured to compare the audio signal to the comparison signal by determining differences with respect to a profile of the sound pressure level with varying frequency within the selected characteristic chronological sequence.

13. The system according to claim 10, wherein the characteristic chronological sequence of the audio signal corresponds to at least a portion of a word and/or a word sequence of the driver of the motor vehicle associated with a verbal input command of the driver.

14. The system according to claim 10, wherein the characteristic chronological sequence of the audio signal corresponds to specific discrete points in time.

15. The system according to claim 10, wherein the processing unit is configured to compare the audio signal to the comparison signal using one of (i) a specific frequency section, (ii) a specific frequency, or (iii) a sound pressure level of the audio signal and the comparison signal being compared.

16. The system according to claim 10, wherein the processing unit is configured to standardize the values of the audio signal and/or the comparison signal before the audio signal is compared to the comparison signal.

17. The system according to claim 10, wherein the processing unit is configured to initiate the protective measure as a function of the detecting of the disease, the protective measure comprising one or more of (i) activating a notification in a system of the vehicle, (ii) activating a supporting driving mode, (iii) initiating an emergency stop, (iv) making an emergency call, (v) changing a passenger compartment climate, and/or (vi) disinfecting the vehicle.

18. The system according to claim 10, wherein the processing unit is configured to execute voice recognition to identify the driver, based on the recorded audio signal.

19. A vehicle comprising a system for activating a protective measure in a vehicle based on a detection of a disease within a vehicle, comprising:

at least one microphone of the vehicle configured to generate an audio signal relating to a driver of the vehicle over a time;

at least one processor of the vehicle, operatively coupled to the at least one microphone, wherein the at least one processor processing unit is configured to select a characteristic chronological sequence of the audio signal for executing a time-resolved analysis of the audio signal;

perform a time-resolved frequency transform of the audio signal within the selected characteristic sequence and compute a difference metric between the transformed audio signal and a stored comparison signal previously recorded from the same driver;

detect a disease based on the computed difference metric; and a vehicle control system operatively coupled to the at least one processor and configured to activate a vehicle-implemented protective measure in response to the detected disease.

20. The vehicle according to claim 19, wherein the audio signal comprises data reflecting the change in the frequency and in the sound pressure level over the time, and wherein the processing unit is configured to compare the audio signal to the comparison signal by determining differences with respect to a profile of the sound pressure level with varying frequency within the selected characteristic chronological sequence.

* * * * *